United States Patent [19]

Powell

[11] Patent Number: 4,944,919

[45] Date of Patent: Jul. 31, 1990

[54] LOW TEMPERATURE STERILIZER

[75] Inventor: Anthony D. Powell, Lima, N.Y.

[73] Assignee: MDT Corporation, Torrance, Calif.

[21] Appl. No.: 54,786

[22] Filed: May 27, 1987

[51] Int. Cl.⁵ ............................................... A61L 2/06
[52] U.S. Cl. ....................................... 422/26; 422/33;
    422/39; 422/107; 422/109; 422/110; 422/295
[58] Field of Search ................ 422/3, 26, 33, 39, 107, 422/109, 110, 295

[56] References Cited

U.S. PATENT DOCUMENTS

| | | | |
|---|---|---|---|
| 4,203,947 | 5/1980 | Young et al. ...................... | 422/26 X |
| 4,238,447 | 12/1980 | Wolff ................................... | 422/26 |
| 4,261,950 | 4/1981 | Bainbridge et al. ................. | 422/26 |
| 4,296,067 | 10/1981 | Näsman et al. ...................... | 422/26 |
| 4,309,381 | 1/1982 | Chamberlain et al. .............. | 422/3 |
| 4,372,916 | 2/1983 | Chamberlain et al. .............. | 422/3 X |
| 4,395,383 | 7/1983 | Kackos ................................ | 422/26 X |
| 4,497,773 | 2/1985 | Kuelzow et al. ..................... | 422/26 |
| 4,687,635 | 8/1987 | Kaehler et al. ...................... | 422/3 X |

Primary Examiner—Robert J. Warden
Assistant Examiner—Lynn Kummert
Attorney, Agent, or Firm—Trask, Britt & Rossa

[57] ABSTRACT

An apparatus for exposing objects to saturated steam at subatmospheric pressure is computer controlled during a conditioning phase prior to the commencement of an exposure phase to apply vacuum to a sealed chamber while steam is simultaneously being injected to that chamber. The fluid stream flowing through the chamber sweeps air and condensate from the chamber and creates a partial vacuum within the chamber. The steam flow rate is controlled to establish the desired exposure temperature within the chamber. Vacuum is controlled to establish an exposure pressure at which steam is saturated at the exposure temperature. The exposure phase commences after the exposure temperature and pressure are established within the chamber.

11 Claims, 4 Drawing Sheets

LOW TEMPERATURE STERILIZER

BACKGROUND OF THE INVENTION

This invention relates to an apparatus of the type used to subject culture media and/or instruments to low temperatures below 100° Centigrade for predetermined time periods; also referred to as low temperature sterilization.

One method in the prior art for providing low temperature sterilization is described in U.S. Pat. No. 4,395,383. Such prior art device wastes large amounts of energy in the form of condensed steam which is continuously passed to drain. Additionally, this device requires numerous control in the sensing mechanism in order to get the chamber to its working temperature and maintain the chamber at such temperature.

Co-pending patent application, serial no. 901,230, filed Aug. 28, 1986 and continuation-in-part filed thereafter (which is currently owned by the assignee of this application) discloses an apparatus and method for low temperature sterilization wherein steam is introduced into a sterilization chamber in response to a temperature being sensed. In one aspect of the invention steam is introduced into the chamber until reaching a preselected temperature. A vacuum is applied to the chamber to lower the pressure in the chamber until reaching a second preset temperature. Steam is allowed to reenter the chamber to raise the temperature to the preselected temperature. This sequence is repeated until the temperature is stabilized and the exposure phase begins. This method is relatively slow in bringing the temperature of the chamber to the preselected exposure temperature and sometimes inconsistant if a previous cycle had recently been completed. A variation of this method was to pull a deep vacuum and then let the alternating steam and vacuum raise the pressure to the preselected operating temperature. This method was consistent but very slow, especially for temperatures above 90° wherein a slight vacuum was required.

Applicant has invented a new method and apparatus wherein the conditioning phase of the sterilization cycle is both fast and consistent.

SUMMARY OF THE INVENTION

In one aspect of the present invention there is provided an apparatus for providing a low temperature environment at a substantially constant uniform temperature. The apparatus comprises a closed sterilization chamber having an inlet and an outlet. The inlet of the chamber is connected to a source of steam. Temperature sensing means is provided for determining the temperature of the chamber and a pressure sensing means is provided for determining the pressure within the chamber. During initial conditioning of the chamber steam is allowed to enter the chamber in response to a preselected temperature sensed by the temperature sensor and a vacuum source is applied to the outlet of the chamber in response to the pressure sensed by the pressure sensing means. During the conditioning phase a vacuum is being applied to the chamber until the pressure within the chamber is drawn at about the pressure for saturated steam for the preselected temperature. Means are also provided for stopping the entrance of the steam within the chamber when the preselected temperature is reached.

In another aspect of the present invention there is provided a method of providing low temperature sterilization in a closed chamber having an inlet and outlet comprising the steps of:
monitoring the temperature of the chamber;
monitoring the pressure within the chamber;
providing steam to the inlet of the chamber in response to the temperature therein;
providing a vacuum during the initial conditioning phase to the outlet of the chamber so as to bring the pressure within the chamber at about the pressure for saturated steam for a preselected environmental temperature in the chamber.

DETAILED DESCRIPTION OF THE INVENTION

Figure 1:
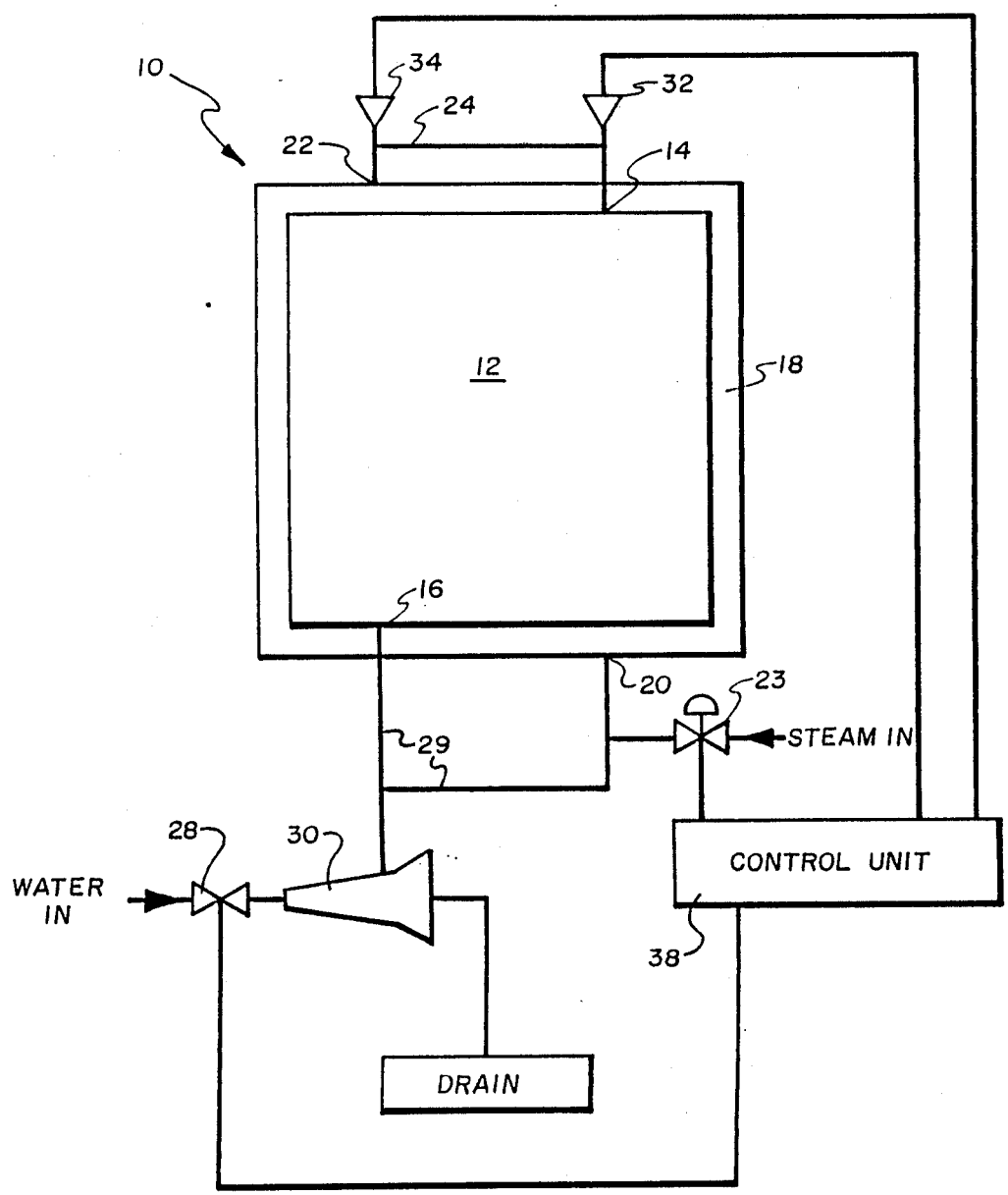
FIG. 1 is a diagrammatical representation of an apparatus made in accordance with the present invention.

Referring to FIG. 1 there is illustrated a diagrammatic representation of a low temperature sterilizing apparatus 10 made in accordance with the present invention for providing low temperature sterilization. For the purpose of this invention, low temperature sterilization shall mean temperatures below 100° C., preferably in the range of about 76° C. to 99° C. The apparatus 10 comprises a sterilization chamber 12 having an inlet port 14 and an outlet port 16 connected to drain. A jacket chamber 18 surrounds the sterilization chamber 12 and has an inlet 20 for the introduction of steam and an outlet 22 for the removal of air and/or steam from the jacket chamber 18 through passageway 24 to inlet 14 of chamber 12.

A pressure sensor 32 is provided in sterilization chamber 12 to monitor the pressure therein. A temperature sensor 34 is provided in jacket chamber 18 for monitoring the temperature therein which in turn is directly related to the temperature within chamber 12. Generally the temperature of the sterilization chamber 12 is about 2° lower than the temperature within the jacket chamber 18.

The inlet 20 of jacket chamber 18 is connected to a source of steam through valve 23. Inlet 20 is also connected to drain through passageway 29. The outlet 16 of chamber 12 is also connected to drain through passageway 29. A water ejector 30 is connected to outlets 16 and 20 for applying a vacuum to chambers 12 and 18. The output of ejector 30 is connected to drain. Valve 28 regulates the water going to ejector 30. A microprocessor control unit 38 is provided for controlling the operation of the various components and monitoring the various sensors. The microprocessor control unit 38 is connected to the various component and sensors as is customarily done in the prior art and is of the type typically used in the prior art.

The operation of the apparatus 10 will now be discussed in detail. The apparatus 10 goes into an initial conditioning phase. This conditioning phase brings the sterilization chamber up to its working temperature (exposure temperature) generally in the range of 76° C. to about 99° C. During a cold start up of the apparatus 10, steam is brought in through inlet port 20 of jacket chamber 18 and out outlet 22 through passageway 24 into the chamber 12. The entering steam forces the air within the jacket chamber 18 out of outlet 22 and into chamber 12. During this initial conditioning phase a vacuum is applied to outlet 16 of sterilization chamber 12 by any desired means. In the particular embodiment illustrated the vacuum is applied by a water ejector 30. The vacuum pulls the air and steam condensate from the bottom of the chamber 12 at outlet 16. The steam condensate in jacket chamber 18 is also removed by this vacuum. Steam is continually supplied to the chamber 12 until reaching a preset exposure temperature sensed by temperature sensor 34. At the same time steam is allowed to enter, a vacuum is being applied to sterilization chamber 16. A vacuum is applied until the vacuum within the chamber 12 is drawn down to approximately the vacuum required for the preselected low exposure temperature environment selected by the operator. For example, if a low temperature sterilization cycle is to be conducted at 85° Centigrade, the vacuum will be applied to chamber 12 until the vacuum reaches the pressure (vacuum) for saturated steam for 85° C., i.e., about 7.7 psia and for a low temperature sterilization cycle at 92° C., a vacuum would be applied until reaching a pressure of about 11 psia. Accordingly, as the preselected exposure temperature is varied by the operator, the pressure to which the chamber will be drawn to will vary accordingly. Generally during the initial conditioning phase steam and vacuum are both continuously being applied to chamber 12. However during certain conditions it may not be desirable to maintain this status. For example, if a prior sterilization cycle has recently been completed, only a small amount of steam would be necessary to raise the temperature of the chamber 12 to the preselected operating exposure temperature. Therefore, control unit 38 is programmed so that steam will be stopped from entering chamber 12 if the chamber 12 temperature rises above a preset temperature. This will minimize the possibility of overheating the load. Another undesirable situation may arise if the vacuum being applied is too weak or if the steam pressure is too high in which case it may take too long to reach the appropriate vacuum for the preselected exposure temperature. In this situation the steam is turned off after a preset time, for example, five minutes. Once the temperature and pressure within the chamber stabilizes at its preselected exposure temperature, the applying of a vacuum in response to the pressure sensed in chamber 12 is no longer necessary. The sterilizer then starts its exposure phase. At this time, the apparatus can be operated in a manner as previously known in the prior art, preferably as discussed in co-pending U.S. patent application, Ser. No. 901,230, filed Aug. 28, 1986, and continuation-in-part application filed concurrently with this application which are both hereby incorporated by reference. In these applications steam and vacuum is supplied to the sterilization chamber in response to a single monitoring means. In the particular embodiment of the present invention, the monitor means is temperature sensor 34. A vacuum is applied to chamber 12 by water ejector 30 so as to regulate the steam in chamber 12 about its saturation point for the preselected exposure temperature. Steam is allowed to enter the chamber when the temperature drops below a predetermined amount below the preselected exposure temperature and a vacuum is applied when the temperature rises a predetermined amount above the preselected exposure temperature. The apparatus preferably alternates between the entrance of steam and the applying of a vacuum.

Figure 2:
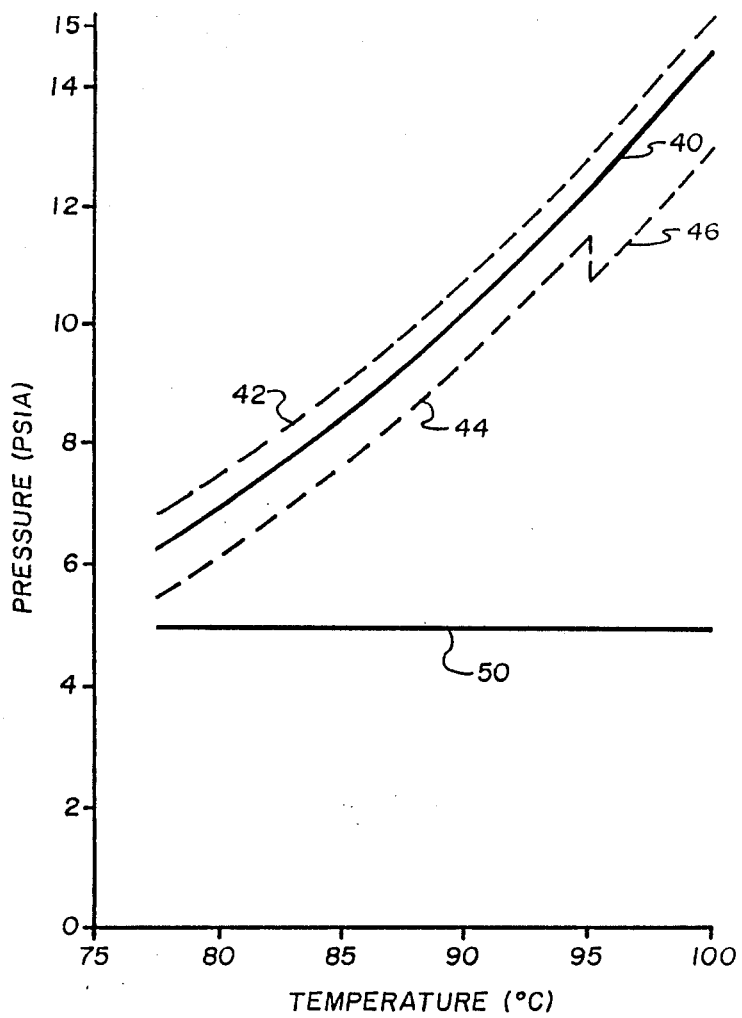
FIG. 2 is a graphical representation of the saturated steam curve, pressure vs. temperature.

Referring to FIG. 2 there is illustrated the pressure temperature steam saturation curve 40 (as shown in solid line). In the practice of the present invention it is preferred that the level of vacuum to which the chamber is drawn down to during the initial conditioning phase for temperatures below 99° C. be no more than about ¼ psi above the vacuum required for the selected exposure temperature (as illustrated by dash line 42) and preferably not greater than ⅛ psi. For low temperature exposure temperatures from about 76° to about 95° C., preferably the pressure in chamber 12 is taken down no greater than about 1½ psi below the pressure for saturated steam at the selected temperature (as shown by dash line 44). For temperature above 95° C., the vacuum in chamber 12 is taken down within about 3 psi below the pressure for saturated steam at the selected exposure temperature (as illustrated by dash line 46). The dash lines 42, 44 and 46 indicate the general boundary that the pressure should be approximately maintained for any desired temperature.

In a sterilizer of the type previously discussed in prior patent application serial no. 901,230, a vacuum was pulled down to about 4.8 psia or as illustrated by curve 50 for all temperature settings. As can be seen from FIG. 2 a considerable amount of excess vacuum was applied to chamber 12 in comparison to the present invention.

Figure 3:
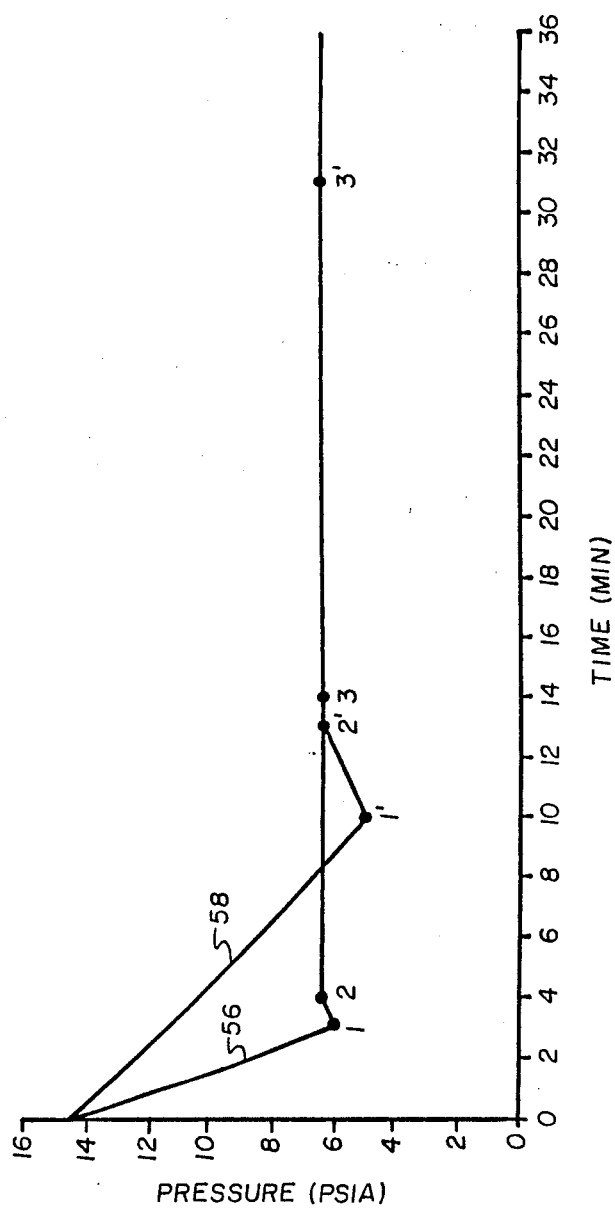
FIG. 3 graphically illustrates the pressure vs. time curves for an apparatus made in accordance with the present invention and an apparatus of the prior art for a 78° C. exposure temperature.
Figure 4:
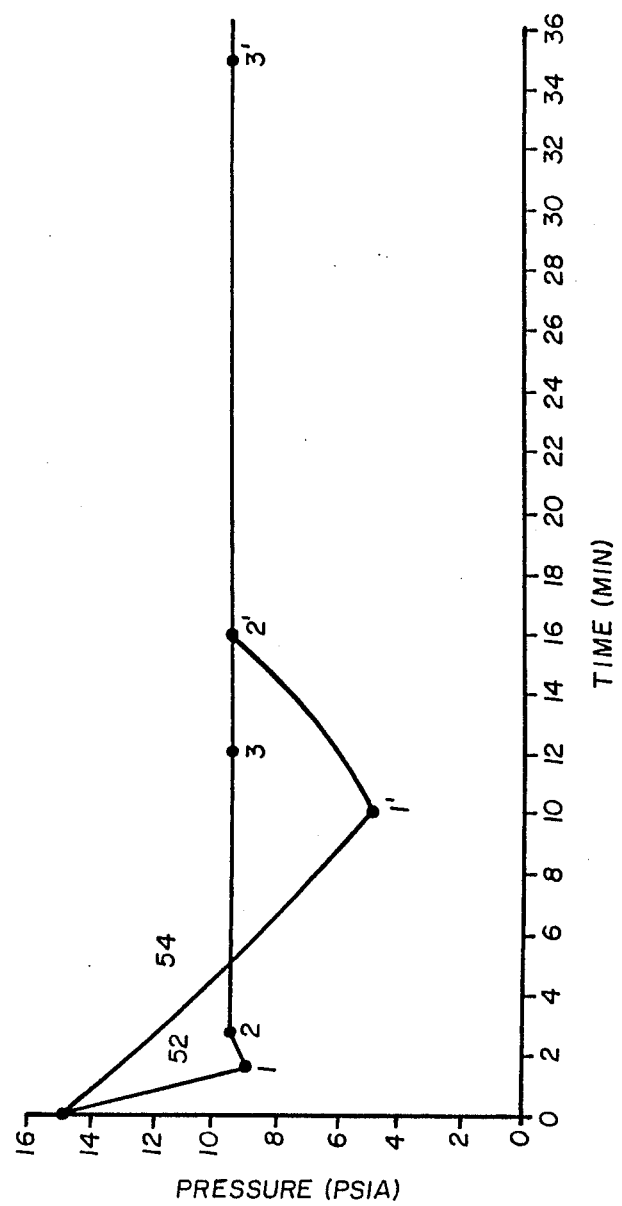
FIG. 4 graphically illustrates the pressure vs. time curves for an apparatus made in accordance with the present invention and an apparatus of the prior art for an 88° C. exposure temperature.

Referring to FIG. 3 there is illustrated in graphical form the pressure vs. time curve for an apparatus made in accordance with the present invention and for an apparatus made in accordance with the prior art for a low temperature sterilization cycle at 78° C. Curve 52 indicates a low temperature sterilization cycle of 78° C. for an apparatus made in accordance with the present invention. Curve 54 indicates a low temperature sterilizing cycle of 78° C. for an apparatus of the prior art. Referring to FIG. 4, curve 56 indicates a curve for a low temperature sterilization cycle of 78° C. for an apparatus made in accordance with the present invention and a curve 58 for sterilization cycle of 88° C. for an apparatus of the prior art. All four curves 52, 54, 56 and 58 were obtained using the same apparatus and same identical load conditions.

Referring back to FIG. 3, curve 52 starts at approximately 14.7 psi at point 0 and continues on to point 1 which is slightly below the pressure required for 88° C. Thereafter the pressure in the chamber 12 is allowed to increase to the pressure which corresponds to the working temperature. In the particular instance this is about 10 psia and is the pressure about which the sterilization chamber is controlled about in order to obtain the appropriate low temperature sterilization temperature. Point 3 indicates the point in time wherein the load in the sterilizer reaches the preset low temperature sterilization temperature. Therefore, it can be seen from curve 52 that it takes approximately 3 minutes for the chamber to reach the operating temperature and approximately a total of about 12 minutes wherein the load reaches the exposure temperature. After point 3 the load is continued to be subjected to the low temperature condition as long as desired as is commonly done in the prior art. Referring to curve 54 (identified by points 0, 1', 2' and 3'), which is the curve for the low temperature sterilization of an apparatus made in accordance with the prior art, and more particularly as described in applicant's prior application serial no. 901,230 previously discussed. Curve 54 is drawn down to initial vacuum of approximately 5 psia, which takes approximately 10 minutes (see point 1'). The pressure in chamber 12 is allowed to rise to approximately 10 psi at point 2' which takes an additional 6 minutes. Therefore, it took approximately 16 minutes to reach the exposure temperature in chamber 12 in contrast to the apparatus of the present invention which took approximately 3 minutes (see point 2). Thereafter, the prior art apparatus took an additional 18 minutes to go from point 2' to point 3' (point 3' being the point in time where the load in the sterilization chamber reaches the exposure temperature). As can be seen the time it takes to go from 2' to 3' of curve 54 vs. the time from point 2 to point 3 of curve 52 is considerably longer. This is due to the fact that in the apparatus of the prior art no substantial amount of steam is allowed to enter the chamber during the point from point 0 to point 1. This is in contrast to the present invention where steam is allowed to enter chamber 12 when a vacuum is being applied. Because as steam enters it expands improving the ejector efficiency then condenses providing a vacuum quicker in chamber 12. Additionally, because of the heat coming in during this time period, this helps heat the load within the chamber. Accordingly, the time from point 2 to point 3 is considerably less than the time from 2' to 3'. The same advantage was also experienced for a low temperature exposure cycle of 78° C.

Referring to the curve 56 which comprises points 0, 1, 2 and 3 the numerals indicating like points as previously discussed with respect to curve 52. Curve 56 illustrates an apparatus made in accordance with the present invention. As can be seen the time necessary for the chamber 12 to reach working temperature (point 2) took approximately 4 minutes as opposed to an apparatus of the prior art which is illustrated by curve 58. Curve 58 is identified by points 0, 1', 2' and 3'. The prior art device took approximately 13 minutes to reach an operating temperature within the sterilization chamber 12 of about approximately 78° C. which is in contrast to the approximate 4 minutes of an apparatus according to the present invention. Additionally, an apparatus of the present invention took a total of approximately 14 minutes (point 3) until load reached the exposure temperature as opposed to approximately 31 minutes for an apparatus of the prior art indicated by point 3'. FIGS. 3 and 4 clearly illustrate the tremendous time and energy advantage in which an apparatus made in accordance with the present invention provides over the prior art.

Various changes and modifications may be made to the present invention without departing from the particular scope of the present invention. For example, but not by way of limitation, various sensors, valves and other controls may be provided as is continuously done in the prior art.

What is claimed is:

1. An apparatus for exposing objects to be saturated steam at subatmospheric pressure, comprising:
    a sealed chamber with an inlet and an outlet;
    a source of steam connected to said inlet through first flow control means;
    a source of vacuum connected to said outlet through second flow control means;
    temperature sensing means mounted to sense the temperature within said chamber;
    pressure sensing means mounted to sense the pressure within said chamber; and
    electronic control means operably associated with said first and second flow control means, said temperature sensing means and said pressure sensing means to effect a conditioning phase of operation prior to an exposure phase of operation in a sterilization cycle, said conditioning phase including the steps of:
        simultaneously introducing steam through said first flow control means and applying vacuum through said second flow control means, thereby to establish a fluid flow stream through said chamber;
        operating said first flow control means in response to the temperature sensed by said temperature sensing means, thereby to establish a preselected exposure temperature within said chamber; and thereafter
        operating said second flow control means in response to the pressure sensed by said pressure sensing means to establish an exposure pressure within said chamber at a pressure level at which steam is saturated at said exposure temperature, while continuing to operate said first flow control means to maintain the temperature within said chamber at said exposure temperature.

2. Apparatus according to claim 1, including a jacket chamber surrounding said sealed chamber including an inlet arranged to receive steam from said first flow control means and an outlet arranged to pass steam to said inlet of said sealed chamber.

3. Apparatus according to claim 2 wherein said temperature sensing means is located to directly monitor the temperature within said jacket chamber, thereby indirectly to monitor the temperature within said sealed chamber.

4. Apparatus according to claim 1 wherein said electronic control means is operable to establish an exposure temperature below 100° C.

5. Apparatus according to claim 4 wherein said electronic control means is operable to establish an exposure temperature within the range of about 76° C. to about 99° C.

6. Apparatus according to claim 1 wherein said electronic control means comprises a microprocessor control device.

7. Apparatus according to claim 6 wherein said microprocessor control device is programmed to control said first and second flow control means in response to said temperature sensing means during an exposure phase subsequent to said conditioning phase to provide for the introduction of steam to said sealed chamber when the temperature sensed within said chamber by said temperature sensing means is below said exposure temperature and the application of vacuum to said chamber when the temperature sensed within said chamber is above said exposure temperature.

8. Apparatus according to claim 6 wherein said microprocessor is programmed to operate said second flow control means during the initial portion of said conditioning phase to effect a preliminary pressure within said sealed chamber near but higher than said exposure pressure.

9. Apparatus according to claim 8 wherein said microprocessor is programmed to effect said preliminary pressure at less than about κ psi higher than said exposure pressure.

10. Apparatus according to claim 6 wherein said microprocessor is programmed to establish an exposure temperature within said chamber below about 95° C. and an exposure pressure within said chamber below but within about 1½ psi of the saturation pressure of steam at said exposure temperature.

11. Apparatus according to claim 6 wherein said microprocessor is programmed to establish an exposure temperature within said chamber below about 95° C. and an exposure temperature within said chamber below but within about 3 psi of the saturation pressure of steam at said exposure temperature.

* * * * *

UNITED STATES PATENT OFFICE
CERTIFICATE OF CORRECTION

Patent No. 4,944,919                     Dated   July 31, 1990

Inventor(s)   Anthony D. Powell

It is certified that error appears in the above-identified patent and that said Letters Patent is hereby corrected as shown below:

In Claim 9, column 7, line 1, after "about", delete "k psi" and insert --1/2 psi--.

Signed and Sealed this

Twenty-seventh Day of August, 1991

Attest:

HARRY F. MANBECK, JR.

Attesting Officer

Commissioner of Patents and Trademarks